Figure 1:
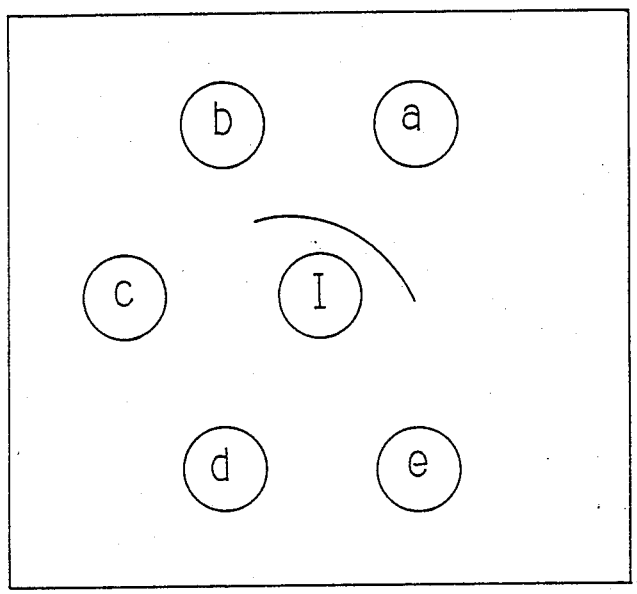

United States Patent [19]

Miyauchi et al.

[11] Patent Number: 4,725,557
[45] Date of Patent: Feb. 16, 1988

[54] PRODUCTION OF FUCOSYL ANTIGENS AND ANTIBODIES FOR RECOGNIZING SAME DETERMINATION OF CANCER ASSOCIATED CARBOHYDRATE LINKAGE USING SAME AND KIT FOR THE DETERMINATION

[75] Inventors: Teruo Miyauchi; Suguru Yonezawa; Masayuki Ozawa; Eiichi Sato; Takashi Muramatsu, all of Kagoshima; Setsuzo Tejima; Taku Chiba, both of Nagoya, all of Japan

[73] Assignee: Otsuka Pharmaceutical Co., Ltd., Japan

[21] Appl. No.: 573,920

[22] PCT Filed: May 28, 1983

[86] PCT No.: PCT/JP83/00169
§ 371 Date: Jan. 19, 1984
§ 102(e) Date: Jan. 19, 1984

[87] PCT Pub. No.: WO83/04311
PCT Pub. Date: Dec. 8, 1983

[30] Foreign Application Priority Data

Jun. 3, 1982 [JP] Japan .................. 57-95787
Jun. 3, 1982 [JP] Japan .................. 57-95788
Jun. 3, 1982 [JP] Japan .................. 57-95789

[51] Int. Cl.$^4$ ........................... G01N 33/531
[52] U.S. Cl. ................... 436/543; 436/519; 424/88; 536/123; 536/124; 514/54; 530/387; 530/411; 530/813

[58] Field of Search ............ 435/7; 424/88; 536/124, 536/123; 514/54; 436/519, 543; 530/411, 813, 387

[56] References Cited

U.S. PATENT DOCUMENTS 4,078,049 3/1970 Felix et al. ............... 436/823
4,238,473 12/1980 Lemieux et al. .......... 424/11

FOREIGN PATENT DOCUMENTS 0069678 1/1985 European Pat. Off.

*Primary Examiner*—Robert J. Warden
*Assistant Examiner*—Stephen C. Wieder
*Attorney, Agent, or Firm*—Larson and Taylor

[57] ABSTRACT

The invention relates to a process for producing a fucosyl antigen charcterized in that an oligosaccharide contaning an α-fucoyransoyl-(1→3)-, -(1→4)- or -(1→6)-galactoyransoyl group and serving as a hapten is reacted wtih a carrier protein to obtain a carbohydrate antigen and to a process for producing from the antigen an antibody having specific reactivity with cells of cancers of the digestive system, especially human colon carcinoma cells, and murine teratocarcinoma cells.

The invention also relates to a method of determining a cancer associated crabohydrate linkage with use of such antibody capable of specifically recognizing specific carbohydrate linkage and to a cancer diagnosing kit containing the antibody.

17 Claims, 3 Drawing Figures

PRODUCTION OF FUCOSYL ANTIGENS AND ANTIBODIES FOR RECOGNIZING SAME DETERMINATION OF CANCER ASSOCIATED CARBOHYDRATE LINKAGE USING SAME AND KIT FOR THE DETERMINATION

TECHNICAL FIELD

The present invention relates to techniques for producing fucosyl antigens and antibodies for recognizing the same, and more particularly to a process for producing carbohydrate antigens containing a specific carbohydrate linkage as a hapten and a process for producing from the antigens antibodies having specific reactivity with cells of cancers of the digestive system, especially human colon carcinoma cells, and murine teratocarcinoma cells. The present invention also relates to a technique for determining cancer associated carbohydrate linkages with use of such antibodies capable of specifically recognizing specific carbohydrate linkages.

At certain stages of cellular differentiation, specific carbohydrate antigens are recently expressed on the surface of mammalian cells. Monoclonal antibodies [Cell, Vol. 14, 775-783 (1978), Proc., Natl., Acad., USA, Vol. 75, No.11, 5565-5569 (1978) and Nature, Vol. 292, 156-158 (1981)] produced by the hybridoma technique using whole cells as the immunogen, and the antibodies present in sera of some patients [Exp. Cell Res., 131, 185-195 (1981)] have been proposed as antibodies which are reactive with such carbohydrate antigens. In the course of our research conducted in connection with the abovementioned reports, we have succeeded in preparing carbohydrate antigens from specific carbohydrate linkages obtained by organic synthesis and used as haptens and also in producing from the carbohydrate antigens antibodies which specifically selectively react with cells of cancers of the digestive system, especially human colon carcinoma cells, and murine teratocarcinoma cells. We have further obtained the novel finding that the antibodies are useful for recognizing and determining carcinoma cells and for diagnosing cancers. The present invention has been accomplished based on these novel findings.

DESCRIPTION OF THE INVENTION

The present invention provides a process for producing a fucosyl antigen characterized in that an oligosaccharide containing an α-fucopyranosyl-(1→3)-, -(1→4)- or -(1→6)-galactopyranosyl group and serving as a hapten is reacted with a carrier protein to obtain a carbohydrate antigen.

The invention further provides a process for producing an antibody for recognizing the fucosyl antigen characterized by administering to a mammal a carbohydrate antigen comprising a complex of a carrier protein and an oligosaccharide containing an α-fucopyranosyl-(1→3)-, -(1→4)- or -(1→6)-galactopyranosyl group, and collecting the resulting antibody.

The invention further provides a method of determining a cancer associated carbohydrate linkage having an α-fucopyranosyl-(1→3)-, -(1→4)- or -(1→6)galactopyranosyl group characterized in that the carbohydrate linkage is determined by a immunoreaction with use of an antibody capable of recognizing the group specifically.

The invention further provides a cancer diagnosing kit containing an antibody capable of specifically recognizing the α-fucopyranosyl-(1→3)-, -(1→4)- or -(1→6)-galactopyranosyl group.

Hereinafter described are the production of fucosyl antigens, production of antibodies from the antigens, cancer diagnosing kit containing the antibody, and determination of cancer associated carbohydrate linkages or cancer diagnosis method with use of the antibody, all according to the present invention.

In producing fucosyl antigens according to the present invention, it is essential to use as haptens oligosaccharides containing an α-fucopyranosyl(1→3)-, -(1→4)- or -(1→6)-galactopyranosyl group. The fucopyranose and galactopyranose, which are essential component sugars of the oligosaccharide, are linked together by α1-3, α1-4 or α1-6 bond, of which the α1-3 bond is especially preferred. The galactopyranosyl group of the oligosaccharide may have attached thereto another carbohydrate linkage. Typical of sugars constituting such linkages is, for example, glucopyranose. The glucopyranose may be attached to the galactopyranose by α or β bond. The component sugars may be D-isomers or L-isomers.

Examples of suitable oligosaccharides are as follows.

* O-α-L-fucopyranosyl-(1→3)-O-β-D-galactopyranosyl(1→4)-α-D-glucopyranose(3'-α-L-fucopyranosyl-αlactose)
* O-α-L-fucopyranosyl-(1→4)-O-β-D-galactopyranosyl(1→4)-α-D-glucopyranose(4'-α-L-fucopyranosyl-αlactose)
* O-α-L-fucopyranosyl-(1→6)-O-β-D-galactopyranosyl(1→4)-α-D-glucopyranose(6'-α-L-fucopyranosyl-αlactose)

These oligosaccharides are known or can be easily prepared by various known methods (Chem. Pharm. Bull. 29 (4) 1076-1082 (1981) and The Third Glycide Symposium, Report Summaries, pp. 90-91, Subject 43 "Synthesis of Human Milk Saccharides", August 1980).

The carrier proteins to be bonded to such oligosaccharides as haptens are a wide variety of natural or synthetic high-molecular-weight proteins which are usually used for preparing antigens and which include, for example, animal serum albumins such as equine serum albumin, bovine serum albumin (BSA), rabbit serum albumin, human serum alubmin, ovine serum albumin, albumen albumin and the like; animal serum globulins such as equine serum globulin, bovine serum globulin, rabbit serum globulin, human serum globulin, ovine serum globulin, alubmen globulin and the like: animal thyroglobulins such as equine thyroglobulin, bovine thyroglobulin, rabbit thyroglobulin, human thyroglobulin, ovine thyroglobulin and the like: animal hemoglobulin such as equine hemoglobulin, bovine hemoglobulin, rabbit hemoglobulin, human hemoglobulin, ovine hemoglobulin and the like; animal hemocyanins: proteins extracted from ascaris [ascaris extracts as disclosed in Japanese Patent Kokai (Laid-Open) No. Sho-16414/1981]; edestin, polylysine, polyglutaminic acid, a lysine-glutaminic acid copolymer, copolymer containing lysine or ornitine; etc.

The hapten (oligosaccharide) can be reacted with the carrier protein by various known methods, for example, by (A) isothiocyanate coupling method, (B) diazo coupling method, (C) amide bonding method, (D) reducing amination method, (E) guanidine coupling method, etc. [Advances in Carbohydrate Chemistry and Biochemistry, Vol. 37, p225-281 (1980), Methods in Enzymology, Vol. 1, Complex Carbohydrates, Part C, p155-175 (1978), Tanpakushitsu Kakusan Koso (Protein Nucleic Acid Enzyme), Vol. 25, No.8, p707-724 (1980) and Archives of Biochemistry and Biophysics, Vol. 205, No.2, p338-395 (1980)].

According to the isothiocyanate coupling method (A), thiophosgene is reacted with a compound obtained by a reducing amination reaction (wherein the hapten is reacted, for example, with β-(p-aminophenyl) ethylamine or like diamine derivative and NaBH$_4$, NaBH$_3$CN or like reducing agent), and a carrier protein is coupled with the resulting isothiocyanate. The reducing amination reaction is carried out favorably in a suitable inert solvent, such as a buffer solution for example of 0.2 mole of calcium phosphate (pH=8), water, physiological saline or methanol, ethanol or like alcohol, at 0° to 40° C. for 3 hours to 3 days. Thiophosgene is reacted with the compound obtained by the amination reaction advantageously in a suitable inert solvent, such as water, 0.1 mole aqueous sodium hydrogencarbonate solution (pH=8) or physiological saline, at −10° C. to room temperature for 30 minutes to 2 hours. Further the reaction between the isothiocyanate and the carrier protein is carried out favorably in a suitable inert solvent, such as water, physiological saline or 0.1 mole aqueous sodium hydrogencarbonate solution (pH=9.5), at −10° C. to room temperature for 15 to 20 hours.

The diazo coupling method (B) is practiced, for example, by reacting sodium nitrite and a diazotizing agent, such as hydrochloric acid or sulfuric acid, with the compound resulting from the reducing amination reaction of the method A to obtain a diazo compound, and coupling a carrier protein with the diazo compound. The diazotization reaction is conducted favorably in an inert solvent, such as water, physiological saline or aqueous solution of hydrochloric acid or like mineral acid, at −10° to −20° C. for 10 to 60 minutes. The carrier protein can be coupled with the diazo compound favorably at −10° to 20° C. in 2 to 6 hours.

The amide bonding method (C) is practiced, for example, by oxidizing the aldehyde group of the hapten with silver oxide or like oxidizing agent to a sugar carboxylic acid, and subjecting the carboxyl group of the acid and the amino group of a carrier protein to an amide bonding reaction. The amide bonding reaction can be effected by the amide bond forming reaction of usual peptide, for example, by dehydration condensation reaction using a dehydrating agent such as 1-ethyl-3-(dimethylaminopropyl)-carbodiimide. This condensation reaction is carried out favorably in a suitable solvent, such as 1 mole sodium acetate buffer solution (pH=5.5) or like buffer solution, at 0° C. to room temperature for 3 to 12 hours.

The reducing amination method (D) is practiced, for example, by reacting the hapten with a carrier protein and a reducing agent, such as NaBH$_4$ or NaBH$_3$CN. This reaction can be carried out under the same conditions as the reducing amination reaction of the method A.

In the foregoing methods A to D, each reagent is used approximately in an equimolar amount, preferably an excessive amount, based on the material.

In this way, the desired carbohydrate antigen (fucosyl antigen) can be produced wherein an oligo-saccharide is bonded to a carrier protein. The carbohydrate antigen resulting from the reaction can be easily isolated and purified, for example, by dialysis, gel filtration, fractionating precipitation or the like. Of the carbohydrate antigens thus produced, preferable are those which comprise 20 to 25 moles, on the average, of oligosaccharide per mole of the carrier protein as bonded thereto.

Antibodies are prepared from the carbohydrate antigens by the usual process, i.e., by administering the antigen to a mammal and collecting the antibody produced in the living body. Mammals useful for preparing antibodies are not particularly limited but can be, for example, rabbit, guinea pig, mouse, sheep, goat, ox or cow, horse, etc. Antibodies are produced, for example, by diluting a predetermined amount of antigen with physiological saline to a suitable concentration, followed, when required, by the addition of incomplete or complete Freund's adjuvant or like adjuvant with the dilution, and administering the resulting suspension or dilution to an animal subcutaneously, intramuscularly, intraperitoneally, intravenously, orally or otherwise, preferably subcutaneously, intraperitoneally or intravenously. The frequency of administration, dose, etc. can be determined suitably in the usual manner. For example, the suspension is subcutaneously given to a rabbit (at a dose of 0.05 to 5 mg calculated as the antigen) every two weeks for 1 to 10 months, preferably 1 to 3 months, for immunization. The antibody is collected by collecting blood from the immunized animal when a large quantity of antibody is produced after the final dose is given, usually 1 to 2 weeks after the administration of the final dose, centrifuging the blood and separating off the serum. The serum may be further puried by a usual method, such as salting out, absorption or affinity chromatography.

The antibody thus purified is one capable of specifically recognizing the α-fucopyranosyl-(1→3)-, -(1→4)- or -(1→6)-galactopyranosyl group. The present invention affords an antibody having high specificity to recognize O-α-L-fucopyranosyl-(1→3)-O-β-D-galactopyranosyl when the hapten used is 3'-α-L-fucopyranosylα-lactose, or a specific antibody which recognizes O-α-L-fucopyranosyl-(1→4)-O-β-D-galactopyranosyl when the hapten is 4'-α-L-fucopyranosyl-α-lactose, or a specific antibody which recognizes O-α-L-fucopyranosyl(1→6)-O-β-D-galactopyranosyl when the hapten is 6'-α-L-fucopyranosyl-α-lactose.

The antibodies prepared by the above method of the invention combine with cells of cancers of the digestive system, such as human colon carcinoma cells, and murine teratocarcinoma stem cells, but do not combine with normal tissues, for example, human normal tissues of the colon mucous membrane, liver, gall bladder, pancreas, lung, thyroid gland, thymus, lymphatic gland, muscle, connective tissue, blood vessel, etc. and murine normal tissues of the small intestine, colon, liver, kidney, epididymis, ovary, etc. This is the feature of the antibodies.

Our research has further revealed that the cells of cancers of the digestive system, especially colon carcinoma cells, produce cancer associated carbohydrate linkages having α-fucopyranosyl-(1→3)-, -(1→4)- or -(1→6)-galactopyranosyl group and that such linkages are also present in body fluids of patients with cancer. Accordingly it is possible to determine the cancer associated carbohydrate linkages in the carcinoma cells or tissues or body fluids by immunoreaction (antigen-antibody reaction) with use of the antibodies which specifically recognize α-fucopyranosyl(1→3)-, -(1→4)- or -(1→6)-galactopyranosyl, thus making it possible to diagnose cancers. The present invention provides a method of determining such cancer associated carbohydrate linkages or of diagnosing cancers and also a cancer diagnosing kit therefor.

The antibody useful for the determination of the cancer associated carbohydrate linkage and for the diagnosis of cancer is any of those obtained as above and capable of specifically recognizing α-fucopyranosyl(1→3)-, -(1→4)- or -(1→6)-galactopyranosyl group. More specifically, useful antibodies are one which recognizes O-α-L-fucopyranosyl-(1→3)-O-β-D-galactopyranosyl (hereinafter referred to as "antibody-I"), one which recognizes O-α-L-fucopyranosyl-(1→4)-O-β-D-galactopyranosyl (hereinafter referred to as "antibody-II"), and one which recognizes O-α-L-fucopyranosyl-(1→6)-O-β-D-galactopyranosyl (hereinafter referred to as "antibody-III"). Of these antibodies, antibody-I is preferred. Examples of cancer associated carbohydrate linkages are glycoproteins and glycolipids having α-fucopyranosyl(1→3)-, -(1→4)- or -(1→6)-galactopyranosyl group.

According to the invention, the cancer associated carbohydrate linkage is determined by a usual method, for example, as follows. When the sample to be used for the determination is cells and/or a tissue section, usual indirect immunoassay is resorted to. According to this method, the antibody of the invention is immunologically reacted with cells suspended in physiological saline or usual phosphate buffer solution (PBS) or like buffer solution or with a tissue section fixed on a glass slide, and the cells or tissue section is thoroughly washed with such a buffer solution and thereafter checked for the presence or absence of the antibody as combined with the sample, by a usual method, i.e., the labelled antibody method, or with use of labelled protein A.

In the case of the labelled antibody method, a labelled antibody against the immunoglobulin (antigens) of the kind of animal used for preparing the antibody of the invention is usable as suitably selected. Examples of useful labelled antibodies are labelled anti-rabbit immunoglobulin G antibody, labelled antimouse immunoglobulin G antibody, labelled anti-goat immunoglobulin G antibody, etc. Labelling agents for such labelled antibodies and labelled protein A are various fluorochromes and enzymatic labelling substances. Typical of useful fluorochromes are fluorescein isothiocyanate (FITC), tetramethylrhodamine isothiocyanate (TRITC), substituted rhodamine isothiocyanates (XRITC), rhodamine B isothiocyanate, dichlorotriazinefluorescein (DTAF) or the like. Examples of useful enzymatic labelling substances are peroxidase (POX), microperoxidase, chymotrypsinogen, procarboxypeptidase, glyceroaldehyde-3-phosphoric acid dehydrogenaze, amylase, phosphorylase, D-Nase, P-Nase, etc. Usable as the antibody or protein A labelled with such an agent is one which is commercially available or which is prepared in the usual manner [Acta. Endocrinol. Suppl., 168, 206 (1972) and Proc. Nat. Acad. Sci., U.S.A., 57, 713 (1967)]. With the present method, cells or a tissue section treated with the present antibody is reacted with a labelled antibody or labelled protein A which has been diluted with the same buffer solution as mentioned above and is then thoroughly washed in the same manner as above. The labelling activity (fluorescence activity or enzymatic activity) present on the cells or tissue section is thereafter determined in the usual manner.

A body fluid is usable also in the usual manner as the sample for determination. Examples of useful body fluids are blood, fluid of cellular tissues, lympth, pleural effusion, ascites, amniotic fluid, gastric juice, urine, pancreatic juice, spinal fluid, saliva, a supernatant obtained by solubilizing cells or a tissue section, followed by centrifuging, etc. The supernatant can be prepared from a homogenate of cells or tissue section or from cells or tissue section solubilized with a solubilizer, by centrifugal separation. Usually the blood to be used is preferably in the form of serum or plasma. About 0.1 to about 10 ml of such body fluid is collected for use in determination.

The method of the invention wherein body fluids are used as samples is conducted preferably in the usual competitive mode of radioimmunoassay (RIA) or enzyme immunoassay (EIA), which can be carried out by the usual procedure. More specifically stated, specified quantities of a standard antigen, labelled antigen and antibody are subjected to competitive reaction in a usual solvent, and the antigen-antibody bonded product (immune complex) and the unbonded antigen are subsequently separated off. The labelling activity of one of them is measured to prepare a standard curve for the standard antigen ot a known concentration. Similarly with use of the sample (body fluid) to be assayed of unknown concentration in place of the standard antigen, the labelling activity concerned is measured. It is then possible to determine the amount of the substance (cancer associated carbohydrate linkage) which is immunosensitive to the antibody and which is contained in the sample, with reference to the standard curve.

A substance (antigen or hapten thereof) immunosensitive to the antibody to be used is usable as the standard antigen. Examples of useful haptens are 3'-α-L-fucopyranosyl-α-lactose when antibody-I is used, 4'-α-L-fucopyranosyl-α-lactose when antibody-II is used, and 6'-α-L-fucopyranosyl-α-lactose when antibody-III is used. Examples of useful antigens are those respectively corresponding to these haptens, such as the combined products of haptens and carrier proteins (e.g. PIP-BSA), like those obtained in the preparation examples of antigens to be given later.

Useful labelled antigens are those obtained by labelling standard antigens with a radioactive substance, such as $^{125}I$ or $^{3}H$, or one of various enzymatic labelling substances exemplified above. The standard antigen can be labelled by introducing radioactive iodine thereinto, for example, in the following manner. The isothiocyanate (bonded product of hapten-isothiocyanate), singly or as combined with a carrier protein, as already described for the production of antigens, or more specifically, 3'-, 4'- or 6'-α-L-fucopyranosyl-α-lactose-PIP, singly or as combined with BSA, as obtained in the preparation example of antigen to be given later, is labelled in the usual manner with use of Bolton-Hunter reagent [J. Biol. Chem., 254, 9349–9351 (1979)]. Further it is possible to iodinate thyrosine with chloramine T by the oxidizing iodination method [Nature, 194, 495 (1962) and Biochem. J., 89, 114 (1963)] and combining the thyrosine with the PIP group by the aforementioned isothiocyanate coupling method, or to similarly iodinate the thyrosine residue of BSA group. Further $^{3}H$ can be introduced into the standard antigen in the usual manner. For example, the standard antigen is subjected to a reducing reaction with use of $NaB^{3}H_{4}$ or is acetylated with $(C^{3}H_{3}CO)_{2}O$ to obtain a labelled antigen. Examples of preferred solvents for the assay system are those which will not adversely affect immunoreaction, such as water, physiological saline, 0.1 mole trishydrochloric acid buffer solution (pH=7.5), 0.1 mole phosphoric acid buffer solution (pH=7.4) and like buffer solutions having a pH of 6 to 7.8. The immunoreaction is conducted in the usual manner at a temperature of up to 45° C., preferably at 4 to 40° C., for about 1 to about 40 hours. The immune complex resulting from the reaction is separated from the unbonded antigen by a known method. For example, the reaction mixture is treated with dextranactive carbon and then centrifuged for separation. When a second antibody against the antibody, for example a rabbit antibody, is used, the mixture is reacted with goat anti-rabbit IgG antibody or the like and thereafter centrifuged.

The determination method will be described below in greater detail with reference to a specific example.

3'-α-L-Fucopyranosyl-α-lactose-PIP (5 to 10 μg) to be obtained in one of the antigen preparation examples to be given below is labelled with $^{125}I$ with use of Bolton-Hunter reagent (at room temperature, for about 60 seconds) to prepare a labelled antigen. 3'-α-L-Fucopyranosyl-α-lactose is used as the standard antigen, and antibody-I as the antibody. A 0.1 mol quantity (about 10,000 cpm) of the standard antigen, 0.1 ml of antibody-I of suitable concentration and 0.1 ml of the standard antigen of varying concentration are incubated at 4° C. for 24 hours in 0.2 ml of 0.1 M phosphate buffer solution (pH=7) containing 0.5 % BSA and 0.02% $NaN_3$. Subsequently 0.1 ml of normal swine serum and 0.5 ml of dextran-active carbon suspension are added to the mixture, which is then allowed to stand at 4° C. for 30 minutes and thereafter centrifuged (3,000 rpm, 30 minutes). Alternatively 0.1 ml of goat anti-rabbit IgG antibody of suitable concentration is added to the mixture, which is then incubated at 4° C. for 24 hours and then similarly centrifuged. In this way, the immune complex obtained and the unbonded antigen are separated from each other. The radioactivity of the complex is measured. The radioactivity is measured at each concentration of the standard antigen, or the percentage of the antibody-labelled antigen bonded product (B) is calculated with the antibody-standard antigen bonding ratio (BO) corresponding to the potency of the antibody taken as 100%, to obtain a standard curve. Similarly the radioactivity or percentage is determined with use of a sample of unknown concentration in place of the standard antigen. From this value the cancer associated carbohydrate linkage in the sample is determined with reference to the standard curve. Further it is possible by the above method to determine cancer associated carbohydrate linkages having 3'-α-L-fucopyranosyl-α-galactopyranosyl and contained in body fluids. Similarly cancer associated carbohydrate linkages contained in body fluids and having 4'-α-L-fucopyranosyl-α-galactopyranosyl or 6'-α-L-fucopyranosyl-α-galactopyranosyl can be determined with use of antibody-II or antibody-III and corresponding labelled antigen and standard antigen.

The determination method can be practiced conveniently by using a kit for determining the quantity of cancer associated carbohydrate linkage in the blood plasma, serum or like body fluid. It is critical that such a kit contain an antibody which undergoes a specific antigen-antibody reaction with the linkage, i.e., antibody capable of specifically recognizing α-fucopyranosyl(1→3)-, -(1→4)- or -(1→6)-galactopyranosyl. Glycerol, bovine serum protein or like stabilizer and/or preservative can be incorporated into the antibody reagent. The antibody reagent is preferably lyophilized. A watersoluble or water-miscible solvent can be contained in the kit. It is also possible to incorporate into the antibody reagent a buffer solution for maintaining the reagent system at a constant pH on reconstitution, and/or a preservative and/or a stabilizer for preventing the deterioration of the sample before use. The buffer solution, which is not an essential component of the kit reagent, is preferably one which will maintain the system at a pH of 6 to 7.8 when practicing the determination method. The reconstituting agent is preferably one containing water, while part or whole of the water can be replaced by a solvent which is miscible with water. Useful solvents which are miscible with water are those which are already known to one skilled in the art, such as glycerin, alcohols, glycols, glycol ethers, etc., which are not limitative.

Cancer associated carbohydrate linkages can be determined advantageously with use of the kit of the invention. A comparison of the level of linkage determined with the corresponding level in normal person affords diagnosis of cancerous tumors of the digestive system or the like, especially colon cancer, in early to terminal stages. Thus the method of the invention is very useful for the early detection of cancers.

The present invention will be described below in greater detail with reference to preparation examples of carbohydrate antigens (fucosyl antigens) and antibodies.

ANTIGEN PREPARATION EXAMPLE 1

(1) Preparation of 3'-α-L-fucopyranosyl-α-lactose-phenethylamine derivative

3'-α-L-Fucopyranosyl-α-lactose (0.1 mmol) and 3.5 mmol of β-(p-aminophenyl)ethylamine were placed into a closed container and reacted at room temperature for 15 hours with stirring. To the reaction mixture were added 0.5 ml of pure ethanol first and then 1 ml of pure ethanol having suspended therein 12 mg of sodium borohydride, and the mixture was stirred at room temperature for 5 hours. Subsequently the mixture was diluted with 4 ml of water, and glacial acetic acid was added dropwise to the dilution with ice cooling to adjust the mixture to a pH of 5.6. The ethanol was distilled off in a vacuum, water was added to the mixture to adjust its volume to 5 ml, and the mixture was passed through a Sephadex G-10 column (2.5×100 cm) with use of 1 M acetic acid-pyridine buffer solution (pH=5.0) as an eluent. The eluate was obtained in 5-ml fractions. The neutral sugar of each fraction was determined by phenol sulfuric acid reaction. The absorbancy of each fraction was also measured at $OD_{285}$ nm. The fractions having peaks in a match were collected and freeze-dried.

The frozen sample was dissolved in 2 mM acetic acid-pyridine buffer solution (pH=5.0), and the solution was passed through a Whatman CM 52 column (0.5×20 cm) to elute the unreacted material (3'-α-L-fucopyranosy-α-lactose) with the same buffer solution. The eluate was further subjected to elution with 0.1 N ammonia water. The eluate was fractioned into 20 drops (each about 0.6 ml). Each fraction was checked for neutral sugar and absorbancy at $OD_{285}$ nm in the same manner as above. The fractions having peaks in a match were collected and freeze-dried.

The above procedure gave 3'-α-L-fucopyranosyl-α-lactose-phenethylamine derivative. The sugar composition of the derivative was confirmed by gas chromatography [Biochem. Biophys. Acta., 222, 339–347 (1970)]

and high-speed liquid chromatography [Developmental Biology, 90, 441-444 (1982)].

(2) Preparation of 3'-α-L-fucopyranosyl-α-lactose-p-isothiocyanate-phenethylamine derivative (3'-α-L-fucopyranosyl-α-lactose-PIP)

The 3'-α-L-fucopyranosyl-α-lactose-phenethylamine derivative (25 μmol) obtained above procedure (1) was dissolved in 2 ml of 0.1 M aqueous sodium hydrogencarbonate solution (pH=8.0), the solution was placed over 2.5 ml of chloroform containing 65 μmol of thiophosgene, and the mixture was vigorously agitated for 1 hour. The reaction mixture was placed into a centrifugal sedimentation tube, extracted with 2 ml of chloroform twice, and the excess of thiophosgene was removed. Nitrogen gas was passed through the aqueous layer collected to remove the remaining chloroform.

The above procedure gave 3'-α-L-fucopyranosyl-α-lactose-p-isothiocyanate-phenethylamine derivative in the form of an aqueous solution.

(3) Preparation of carbohydrate antigen (3'-α-L-fucopyranosyl-α-lactose-PIP-BSA) by coupling reaction of 3'-α-L-fucopyranosyl-α-lactose-p-isothiocyanate-phenethylamine derivative and bovine serum albumin.

The aqueous solution obtained by the above procedure (2) was added to an aqueous solution of 0.5 M sodium chloride and 0.1 M sodium hydrogencarbonate (pH=9.5) which contains 0.2 μmol of bovine serum albumin (BSA), and the mixture was reacted at room temperature tor 18 hours with stirring. The reaction mixture was dialyzed against 2 liters of Dulbecco-treated PBS (−) (physiological saline-phosphate buffer solution) to remove the unreacted 3-α-L-fucopyranosyl-α-lactose-p-isothiocyanate-phenethylamine derivative. The dialyzing agent was replaced every 12 hours three times, and the liquid obtained was thereafter subjected to Lowry method and phenol sulfuric acid reaction to quantitatively determine protein and neutral sugar. The result revealed that the carbohydrate antigen obtained contained 3'-α-L-fucopyranosyl carbohydrate linkage bonded to bovine serum albumin (BSA) in a ratio of about 20 moles of the former per mole of the latter.

The liquid containing the desired carbohydrate antigen thus obtained was stored frozen. (The product will be referred to as "antigen-1".)

ANTIGEN PREPARATION EXAMPLE 2

A liquid containing a carbohydrate antigen was prepared in the same manner as in Antigen Preparation Example 1 except that 4'-α-L-fucopyranosyl-α-lactose was used in place of 3'-α-L-fucopyranosyl-α-lactose. The liquid was stored frozen (referred to as "antigen-2").

The carbohydrate antigen was found to contain 4'-α-L-fucopyranosyl carbohydrate linkage bonded to bovine serum alubmin (BSA) in a ratio of about 25 moles of the former per mole of the latter.

ANTIGEN PREPARATION EXAMPLE 3

A liquid containing a carbohydrate antigen was prepared in the same manner as in Antigen Preparation Example 1 except that 6'-α-L-fucopyranosyl-α-lactose was used in place of 3'-α-L-fucopyranosyl-α-lactose. The liquid was stored frozen (referred to as "antigen-3").

The carbohydrate antigen was found to contain 6'-α-L-fucopyranosyl carbohydrate linkage bonded to bovine serum albumin (BSA) in a ratio of about 23 moles of the former per mole of the latter.

ANTIBODY PREPARATION EXAMPLE 1

Complete Freund's adjuvant (1 ml) containing 0.4 mg of antigen-1 obtained in Antigen Preparation Example 1 was injected into the footpads of a New Zealand white rabbit. Three weeks thereafter, the same amount of complete Freund's adjuvant containing antigen-1 was injected. This procedure was repeated every 2 weeks 3 times. Ten days after the last injection, the blood was collected from the test animal and centrifuged to collect antiserum and obtain the desired antibody, which will be referred to as "antibody-1". Antibody-1 was stored at −70° C. The antiserum was also freeze-dried to obtain antibody-1 in a dry form.

ANTIBODY PREPARATION EXAMPLE 2

An antibody (antiserum) was prepared in the same manner as in Antibody Preparation Example 2 except that antigen-2 obtained in Antigen Preparation Example 2 was used. The antibody will be referred to as "antibody-2".

ANTIBODY PREPARATION EXAMPLE 3

An antibody (antiserum) was prepared in the same manner as in Antibody Preparation Example 3 with the exception of using antigen-3 obtained in Antigen Preparation Example 3. The antibody will be referred to as "antibody-3".

Antibody specificity tests will be described below in detail.

ANTIBODY SPECIFICITY TEST I (1) Cells were centrifuged (500x g), washed twice with an amount (50 times the amount of cells) of phosphate-buffered physiological saline (containing calcium ions and magnesium ions, pH=7.2) and then suspended in the same saline as above to a concentration of 1 % (V/V). Antibodies-1 to-3 obtained in Antibody Preparation Examples 1 to 3, each diluted to 20 times its volume with phosphate-buffered physiological saline (containing calcium ions and magnesium ions), and normal rabbit serum similarly diluted and serving as a control were admixed with 50 μl portions of the suspension respectively. Each mixture was incubated at 4° C. for 1 hour. The cells of each mixture were thereafter washed with an amount (100 times the amount of culture) of phosphate-buffered physiological saline (containing calcium ions and magnesium ions, pH=7.2) and then incubated with 1/10 dilution of FITC-conjugated goat anti-rabbit IgG (product of Miles-Yeda) at 4° C. for 1 hour. Subsequently the cells were washed twice with an amount (100 times the amount of culture) of the same saline (pH=7.2) as above, observed by a fluorescence microscope using epiillumination (Olympus Model BH-RFL-LB, product of Olympus Optical Co., Ltd.) and photographed on Fuji Color Film ASA 100 (product of Fuji Film Co., Ltd.).

(2) A carcinoma of normal tissue was quick-frozen and sectioned in a cryostat (product of American Optical). The section was fixed to a glass slide with acetone for 1 minute to use as a test specimen, which was tested in the same manner as above with use of FITC-goat anti-rabbit IgG-F(ab)'₂ (product of Cappel) in place of FITC-goat anti-rabbit IgG.

Table 1 shows the reactivity between the cells or tissue sections and antibodies-1 to 3 as determined by the test procedures (1) and (2) above. The signs given in Table 1 and representing the reactivity mean the following.

TABLE 1

|  | Antibody | | |
| --- | --- | --- | --- |
|  | 1 | 2 | 3 |
| *Results of test procedure (1) | | | |
| Normal cells | | | |
| Mouse red blood cells | − | − | − |
| Mouse lymphocytes | − | − | − |
| Mouse spleen cells | − | − | − |
| Mouse thymus cells | − | − | − |
| Human red blood cells | | | |
| (Type H) | − | − | − |
| (Type L ea) | − | − | − |
| Mouse teratocarcinoma | | | |
| F-9 | + | − | − |
| SST-M | + | + | + |
| *Results of test procedure (2) | | | |
| Human normal cells | | | |
| Duodenum | − | − | − |
| Liver | − | − | − |
| Gall bladder | − | − | − |
| Pancreas | − | − | − |
| Lung | − | − | − |
| Thyroid gland | − | − | − |
| Thymus | − | − | − |
| Lymph node | − | − | − |
| Muscle | − | − | − |
| Connective tissue | − | − | − |
| Blood vessel | − | − | − |
| Carcinoma cells | | | |
| Human colon adenocarcinoma (Surgically removed fragment) | + | + | + |

+ ... staining
− ... no staining

No staining was observed in the case of normal rabbit serum which was used as a control in place of antibodies-1 to 3. (3) The human colon adenocarcinoma, which was stained by the test procedure (2), was tested with use of antibody-1 in the same manner as the procedure (2) except that the first reaction was carried out in the presence of 0.2 M 3'-α-L-fucopyranosyl-α-lactose, 0.2 M lactose, 0.2 M fucose or 10 mg/ml BSA. 3'-α-L-Fucopyranosyl-α-lactose was found to have diminished the stain, but no change was found in the stain in the case of lactose, fucose and BSA.

ANTIBODY SPECIFICITY TEST II

Antibodies-1 to 3 were checked for specificity by Ouchterlony double-diffusion analysis as follows. One percent agar gel (containing 2% Triton X-100, 0.15 M NaCl, 50 μg/ml of phenylmethylsulphonyl fluoride and 0.05% NaN$_3$ in 0.01 M TrisHCl buffer (pH=7.6)) was placed on a slide glass. The antibody was placed at the center, and 3'-α-L-fucopyranosyl-α-lactose-PIP-BSA, 4'-α-L-fucopyranosyl-α-lactose-PIP-BSA, 6'-α-L-fucopyranosyl-α-lactose-PIP-BSA, α-lactose-PIP-BSA and BSA, each in an amount of 20 μg and in the form of an aqueous solution, were placed at peripheral portions for diffusion test.

Figure 2:
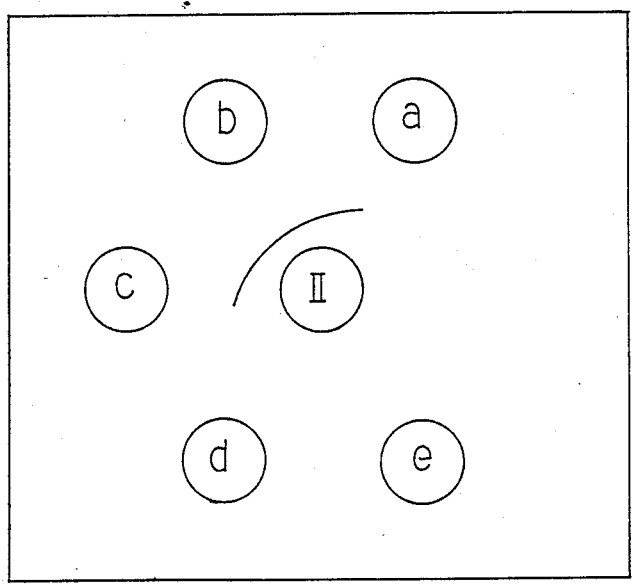
Figure 3:
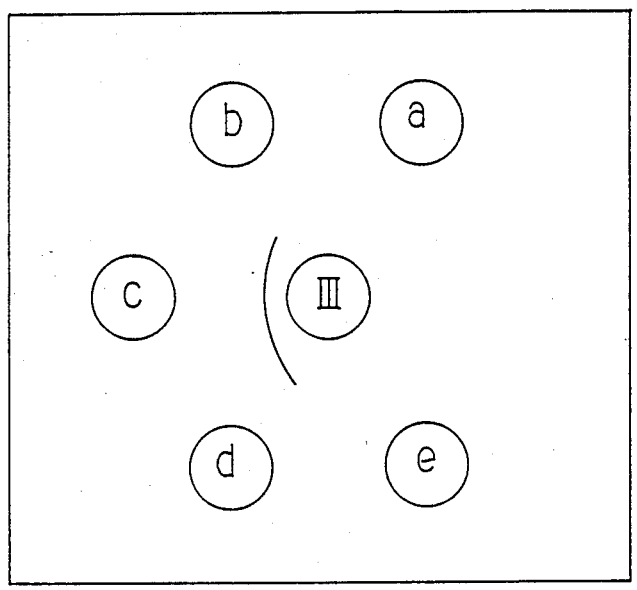

FIGS. 1 to 3 show the results. FIG. 1 shows antibody-1 as diffused, FIG. 2 shows antibody-2 as diffused, and FIG. 3 shows antibody-3 as diffused. Indicated at (a) in these drawings is 3'-α-L-fucopyranosyl-α-lactose-PIP-BSA, at (b) 4'-α-L-fucopyranosyl-α-lactose-PIP-BSA, at (c) 6'-α-L-fucopyranosyl-α-lactose-PIP-BSA, at (d) α-lactose-PIP-BSA, and at (e) BSA. The drawings reveal the following. Antibody-1 forms a precipitation line with 3'-α-L-fucopyranosyl-α-lactose-PIP-BSA but forms no precipitation line with the other antigens. Antibody-2 forms a precipitation line with 4'-α-L-fucopyranosyl-α-lactose-PIP-BSA but no precipitation line with the other antigens. Antibody-3 forms a precipitation line with 6'-α-L-fucopyranosyl-α-lactose-PIP-BSA but no precipitation line with the other antigens. Antibody-2 used for the above test was so treated before the test that 0.4 mg of BSA was added to 1 ml of the antibody obtained in the corresponding preparation example, and the mixture was then allowed to stand overnight at 4° C. and thereafter centrifuged to obtain a supernatant. The supernatant thus made free from anti-BSA antibody was used.

We claim:

1. A carbohydrate antigen comprising a complex of a carrier protein and an oligosacoharide selected from the group consisting of 3'-α-L-fucopyranosyl-α-lactose, 4'-α-L-fucopyranosyl-α-lactose and 6'-α-L-fucopyranosyl-α-lactose.

2. The carbohydrate antigen as defined in claim 1 in which said oligosaccharide is 3'-α-L-fucopyranosyl-α-lactose.

3. The carbohydrate antigen as defined in claim 1 produced by binding the oligosaccharide with the carrier protein.

4. An antibody which is characterized by specifically recognizing an antigen selected from the group consisting of O-α-L-fucopyranoayl-(1→?3)-, -(1→4) and- (1→6) -O-α-D-galactopyranosyl group.

5. An antibody specific for the antigen of claim 1.

6. The antibody as defined in claim 4 in which said antibody is produced by administering to a mammal the carbohydrate antigen of claim 1 and collecting the resulting antibody.

7. The antibody as defined in claim 6 which specifically recognizes O-α-L-fucypyranosyl-(1→3)-O-β-D-galactopyranosyl group.

8. The antibody as defined in claim 4 which specifically recognizes a cancer associated carbohydrate linkage having a group selected from the group consisting of O-α-fucopyranosyl-(1→3)-, -(1→4)- and -(1→6)-O-β-D-galactopyranosyl group.

9. The antibody as defined in claim 8 in which said cancer associated carbohydrate linkage is produced by a human colon carcinoma cell or a murine teratocarcinoma cell.

10. The antibody as defined in claim 6 in which there is administered to a rabbit a carbohydrate antigen produced by reacting 3'-α-L-fucopyranosyl-α-lactose with bovine serum albumin according to an isothicyanate coupling method.

11. The antibody as defined in claim 6 in which there is administered to a rabbit a carbohydrate antigen produced by reacting 4'-α-L-fucopyranosyl-α-lactose with bovine serum albumin according to an isothiocyanate coupling method.

12. The antibody as defined in claim 6 in which there is administered to a rabbit a carbohydrate antigen produced by reacting 6'-α-L-fucopyranosyl-α-lactose with bovine serum albumin according to an isothiocyanate coupling method.

13. A method of determining a cancer associated carbohydrate linkage having a group selected from the group consisting of an O-β-fucopyranosyl-(1→3)-, -(1→4)- and -(1→6)O-β-D-galactopyranosyl group which comprises contacting the antibody of claim 4 with a boilogical sample and determining the presence or absence of the antibody combined with the sample as an indication of the presence of a cancer associated linkage selected from the group consisting of O-α-fucopyranosyl(1→3)-, -(1→4)- and -(1→6)-O-β-D-galactopyranosyl group.

14. The method as defined in claim 13 in which the antibody is the antibody of claim 6.

15. A cancer diagnosing kit comprising a container containing the antibody of claim 4.

16. A cancer diagnosing kit comprising a container containing the antibody of claim 5.

17. A cancer diagnosing kit comprising a container containing the antibody of claim 6.

* * * * *